United States Patent [19]
Fussman

[11] Patent Number: 5,910,134
[45] Date of Patent: Jun. 8, 1999

[54] DEVICE FOR DILATING A PUNCTURE HOLE IN A BODY AND FOR GUIDING THE INSERTION OF AN ELONGATED MEMBER INTO THE BODY

[76] Inventor: Arie Fussman, 2 Manitou Falls Terrace, Sparta, N.J. 07871

[21] Appl. No.: 08/982,749

[22] Filed: Dec. 2, 1997

Related U.S. Application Data

[63] Continuation-in-part of application No. 08/811,497, Mar. 5, 1997, Pat. No. 5,713,868.

[51] Int. Cl.⁶ .................................................. A61M 5/178
[52] U.S. Cl. ........................... 604/164; 604/116; 604/264
[58] Field of Search ..................................... 604/164, 166, 604/116, 264, 280

[56] References Cited

U.S. PATENT DOCUMENTS

| | | | |
|---|---|---|---|
| 4,027,668 | 6/1977 | Dunn | 128/214 R |
| 4,769,005 | 9/1988 | Ginsburg et al. | 604/53 |
| 5,171,225 | 12/1992 | Sterrett | 604/116 X |
| 5,665,069 | 9/1997 | Cumer et al. | 604/116 |

FOREIGN PATENT DOCUMENTS

| | | |
|---|---|---|
| 4138743 | 4/1993 | Germany . |
| 9417574 | 3/1996 | Germany . |
| 9208513 | 5/1992 | WIPO . |

*Primary Examiner*—John D. Yasko
*Attorney, Agent, or Firm*—David L. Davis

[57] ABSTRACT

A plastic device for inserting a catheter or the like into a body, wherein the forward end of the device acts as a dilator and has an offset axial opening along one side for a relatively small needle to pass through. The main portion of the device has a lumen for holding a catheter or the like. The forward end of the lumen is terminated by a slanted guide wall. The device eliminates the need for a separate guidewire and allows the use of a small diameter needle to minimize damage to the body wall.

15 Claims, 5 Drawing Sheets

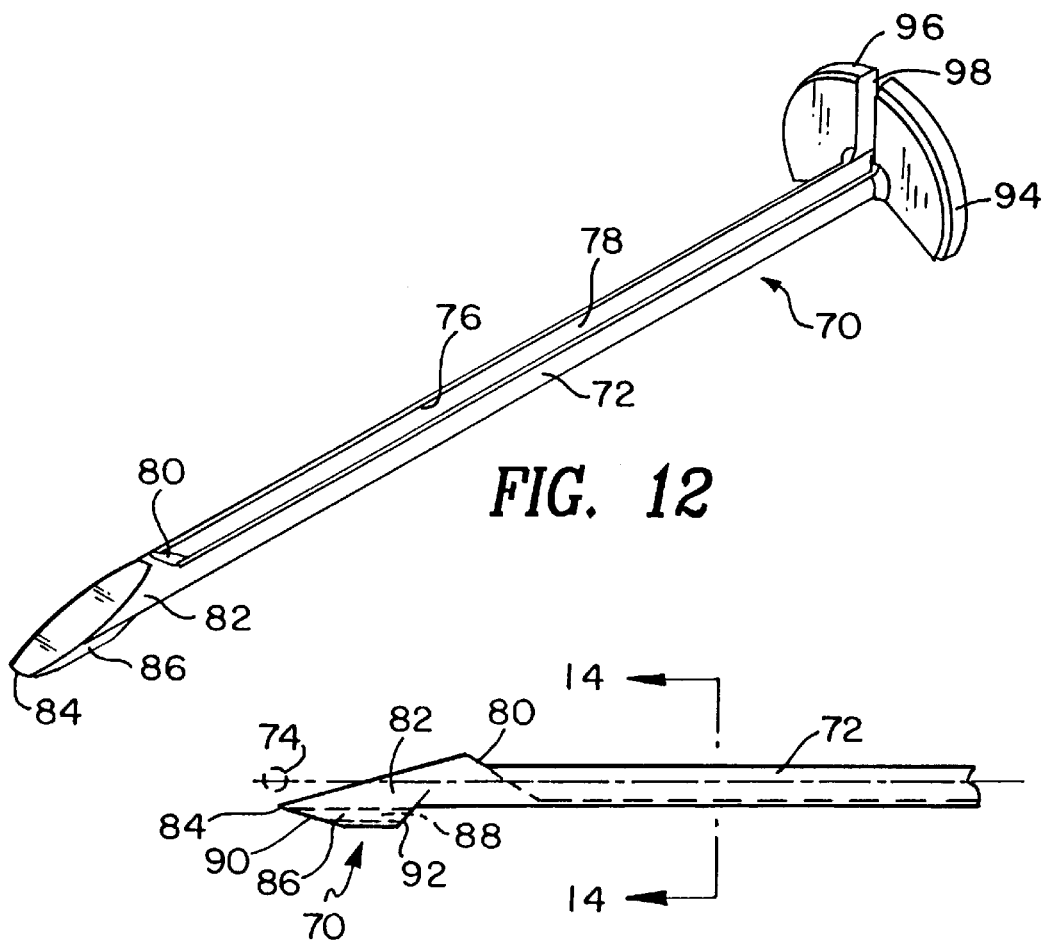
FIG. 12
FIG. 13
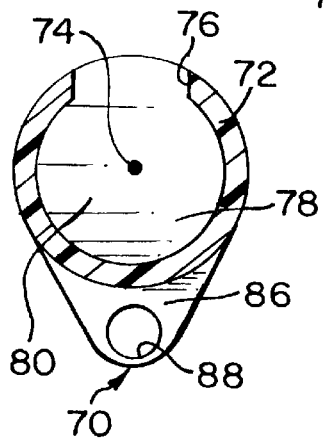
FIG. 14
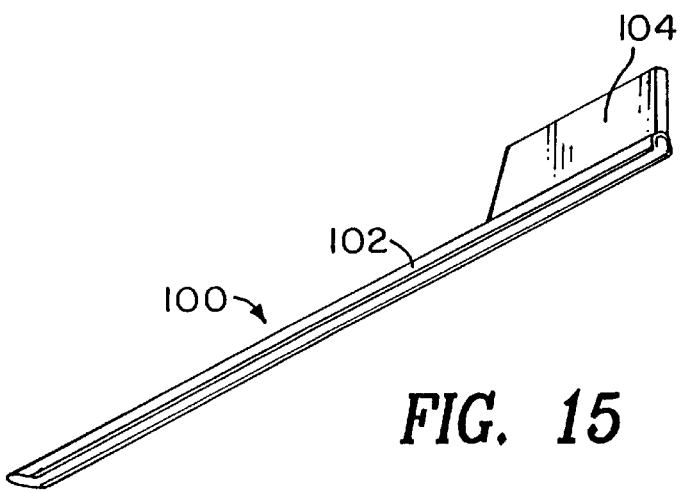
FIG. 15

DEVICE FOR DILATING A PUNCTURE HOLE IN A BODY AND FOR GUIDING THE INSERTION OF AN ELONGATED MEMBER INTO THE BODY

This application is a continuation-in-part of application Ser. No. 08/811,497, filed Mar. 5, 1997, now U.S. Pat. No. 5,713,868.

BACKGROUND OF THE INVENTION

This invention relates to the insertion of an elongated member, such as a catheter, into a body and, more particularly, to an improved device for both dilating a puncture hole in the body and for subsequently providing a guide for the insertion of an elongated member into the body through the puncture hole.

In the following discussion, specific reference will be made to inserting a catheter into a blood vessel. However, it will be appreciated that similar problems arise when inserting other elongated members into a body. Thus, guidewires, optical fibers, stents, etc., are often inserted into a body by forming a puncture hole and guiding such a member into the body through the puncture hole. Accordingly, the present invention has been developed to aid in the insertion of any such elongated member into a body, and use of the term "catheter" is intended to cover all such elongated members.

Vascular dilators are commonly used when inserting a catheter into a blood vessel in order to widen the hole formed by the initial needle or scalpel puncture so that the use of the dilator gradually enlarges the hole. In a typical procedure, a hollow needle is percutaneously inserted into the blood vessel and an elongate, slender guide member, such as a guidewire, is advanced through the interior of the hollow needle into the blood vessel. The needle is then removed over the guide member, leaving the guide member in place in the blood vessel and extending proximally out of and through the patient's skin. The hole left by the needle in the blood vessel typically is too small to permit the catheter to be passed therethrough. A dilator is provided to widen the hole. Dilators commonly are in the form of a flexible plastic tube having a guide member lumen adapted to be passed over the guide member. The dilator is of uniform wall thickness except for a distal portion which tapers in a distal direction to the circular distal outlet opening at the distal end of the dilator. The wall thickness of the dilator at the distal tip is relatively thin to facilitate its entry into the hole made by the needle. As the dilator is advanced over the guide member through the puncture hole, the tapered distal portion presents a progressively wider diameter to the puncture hole, thus gradually enlarging the hole. The dilator is then removed and the catheter is advanced over the guidewire and through the enlarged puncture hole into the blood vessel. The guide member is then withdrawn, leaving the percutaneously placed catheter in place in the blood vessel. This procedure possesses a number of disadvantages. For example, to accommodate the guide member, a relatively large needle is required to penetrate the wall of the blood vessel. Also, a disposable guide member is required.

It would therefore be desirable to provide a catheterization device wherein only a relatively small diameter needle is utilized and no separate guide member is needed.

SUMMARY OF THE INVENTION

The applicant has realized that the problem with the prior art devices arises because all elements are arranged axially concentric. Thus, the guidewire is concentrically within the needle, the dilator concentrically surrounds the needle, and the catheter concentrically surrounds the needle. Therefore, the present invention provides an improved device in which the axis of the puncturing needle is offset from the axis of the catheter.

According to the present invention, a device is constructed in which a relatively small needle may be utilized and no separate guide member is needed. The inventive device comprises a unitary dilator member. The dilator member has an elongated body portion with an outer wall defining a substantially uniform first lumen adapted for receiving a catheter or other elongated member therein. The body portion has an elongated opening longitudinally disposed in the outer wall and communicating with the first lumen. The dilator member further has a forward portion extending forwardly of the body portion and tapering inwardly to a front tip. The forward portion has a second lumen axially offset from the first lumen and adapted for receiving a needle therein with the forward tip of the needle extending forwardly of the front tip and the rear of the needle extending rearwardly alongside the dilator member body portion.

In accordance with an aspect of this invention, the first lumen is open at the rear end of the body portion and the forward end of the first lumen is terminated by a guide wall extending from the bottom of the first lumen opposite the elongated opening and ascending obliquely toward the forward end of the elongated opening.

In accordance with another aspect of this invention, the second lumen is tapered inwardly toward the front tip.

In accordance with a further aspect of this invention, a substantial portion of the length of the body portion forwardly from its rear end is substantially cylindrical and the forward portion of the dilator member extends beyond an axial projection of the cylindrical body portion. At least the lateral opening of the second lumen is in that part of the forward portion which extends beyond the axial projection.

In accordance with yet another aspect of this invention, the first lumen has a circular arcuate shape in cross-section with a diameter sufficiently larger than the diameter of a catheter received therein so that the received catheter has sufficient clearance to move longitudinally within the first lumen. The angle subtended by the first lumen is such that the width of the elongated opening is less than the diameter of the received catheter.

In accordance with still another aspect of this invention, the first and second lumens are substantially parallel each to the other.

BRIEF DESCRIPTION OF THE DRAWINGS

The foregoing will be more readily apparent upon reading the following description in conjunction with the drawings in which like elements in different figures thereof are identified by the same reference numeral and wherein:

FIG. 12 is a perspective view of an alternate embodiment of a catheterization device according to this invention;

FIG. 13 is a partial side view of the catheterization device shown in FIG. 12;

FIG. 14 is a cross sectional view of the catheterization device taken along the line 14—14 in FIG. 13; and FIG. 15 is a perspective view of an alternate embodiment of a cover member for use with the catheterization device shown in FIG. 12.

DETAILED DESCRIPTION

Figure 1:
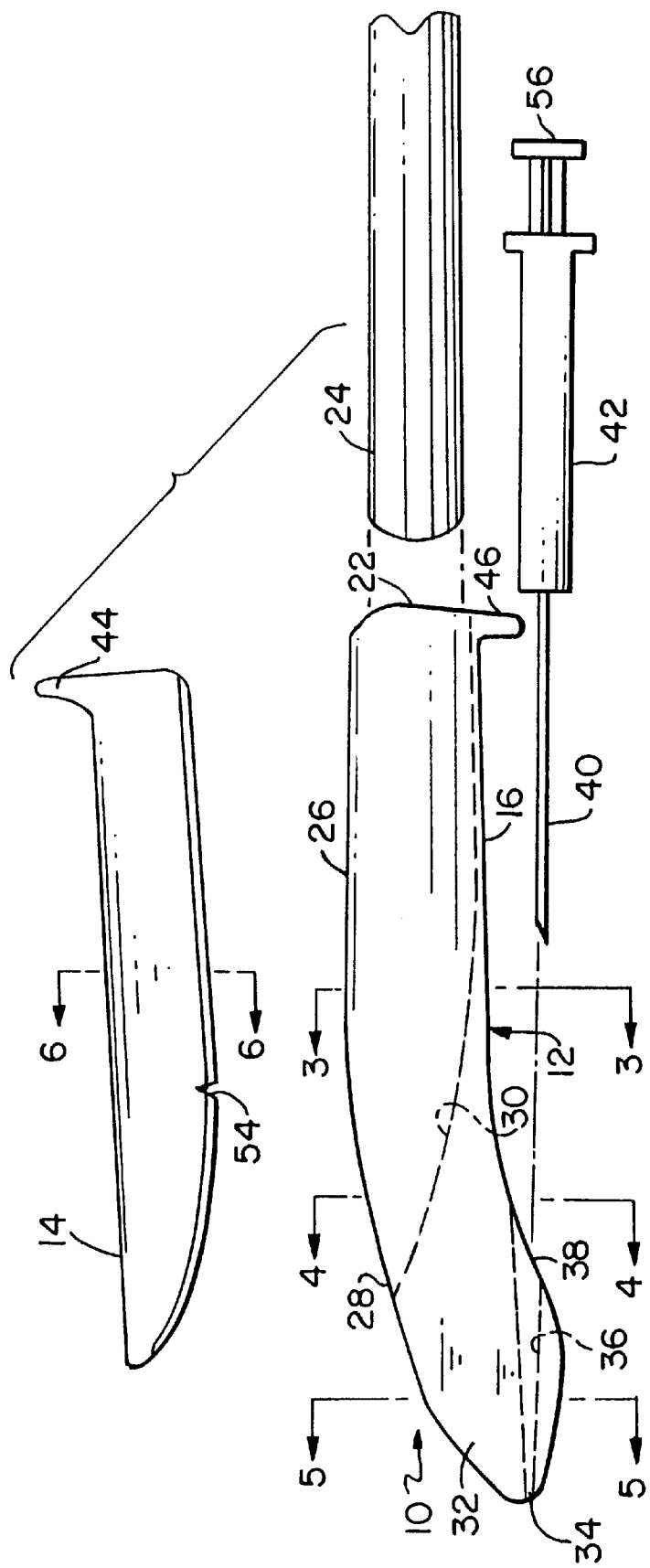
FIG. 1 is an exploded side view showing a catheterization device according to a first embodiment of this invention, along with a hypodermic syringe needle and a catheter.

Referring now to the drawings, a first embodiment of a device according to the present invention, designated generally by the reference numeral 10, comprises a dilator member 12 and a cover member 14. The dilator member 12 is of unitary construction and preferably is formed of a plastic material by a molding process. Similarly, the cover member 14 is also of unitary construction and preferably is formed of a plastic material by a molding process.

Figure 2:
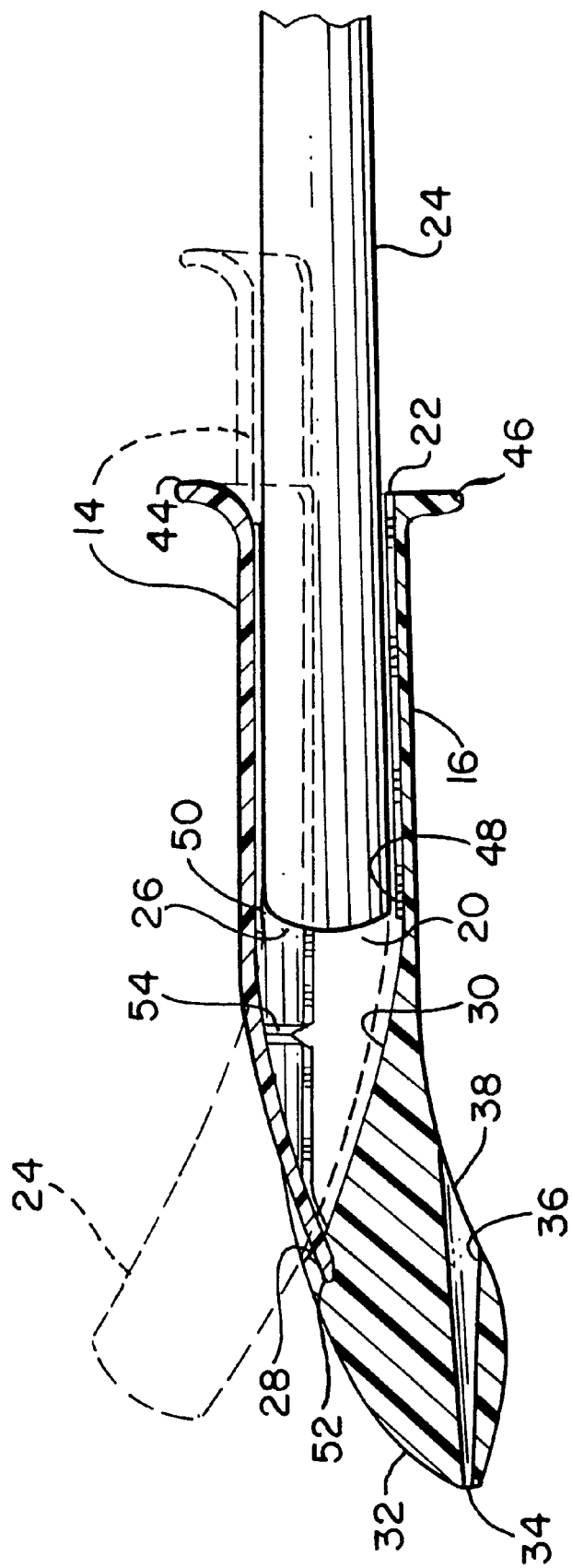
FIG. 2 is a longitudinal cross sectional view of the catheterization device shown in FIG. 1 showing, in solid lines, the catheter inserted in the device and, in broken lines, the guiding of the catheter out of the device.

The dilator member 12 has an elongated body portion 16 having an outer wall 18 which defines a substantially uniform first lumen 20 which is open at the rear end 22 of the body portion 16. The first lumen 20 is adapted for receiving a catheter 24 or other elongated member therein, as best shown in FIG. 2. The body portion 16 has an elongated opening 26 longitudinally disposed in the outer wall 18 which communicates with the first lumen 20 from a forward end 28 of the opening 26 to the rear end 22 of the body portion 16. As will become clear from the following discussion, at least a forward portion of the elongated opening 26 is of sufficient size to allow the catheter 24 to pass therethrough.

Figure 3:
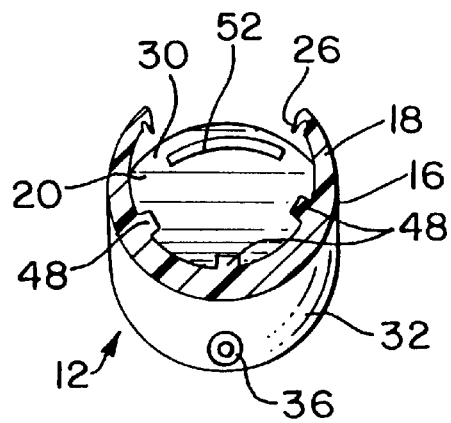
FIG. 3 is a cross sectional view of the dilator member taken along the line 3—3 in FIG. 1.
Figure 4:
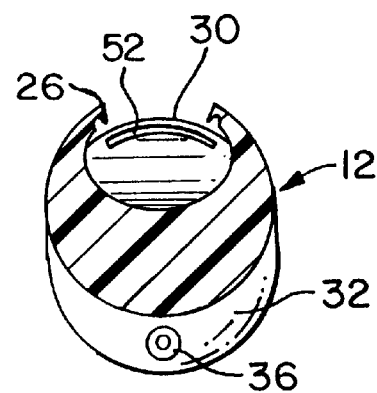
FIG. 4 is a cross sectional view of the dilator member taken along the line 4—4 in FIG. 1.
Figure 5:
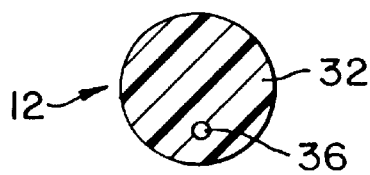
FIG. 5 is a cross sectional view of the dilator member taken along the line 5—5 in FIG. 1.

The forward end of the first lumen 20 is terminated by a guide wall 30 which extends from the bottom of the first lumen 20 opposite the elongated opening 26 and ascends obliquely toward the forward end 28 of the elongated opening 26. A substantial portion of the length of the body portion 16, illustratively from the rear end 22 to the bottom of the guide wall 30, is substantially cylindrical, except for the opening 26. Beginning at the guide wall 30, the dilator member 12 has a forward portion 32 which extends forwardly of the guide wall 30 and tapers inwardly to a front tip 34. This forward portion 32 extends to the opposite side of the dilator member 12 from the elongated opening 26 beyond an axial projection of the cylindrical part of the body portion 16, as is clear from FIG. 3. The forward portion 32 is formed with a second lumen 36 which extends rearwardly from the front tip 34 to a lateral opening 38 on the opposite side of the dilator member 12 from the elongated opening 26. Thus, the second lumen 36 is axially offset from the first lumen 20. The second lumen 36 is adapted for receiving therein the needle 40 of a hypodermic syringe 42, with the tip of the needle 40 extending forwardly of the front tip 34 and the syringe 42 extending rearwardly alongside the body portion 16 of the dilator member 12. Preferably, the second lumen 36 is tapered inwardly toward the front tip 34 so that there is some freedom of movement between the needle 40 and the dilator member 12 when the dilator member 12 is manipulated for insertion into a blood vessel.

Figure 6:
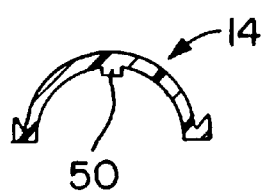
FIG. 6 is a cross sectional view of the cover member taken along the line 6—6 in FIG. 1.
Figure 8:
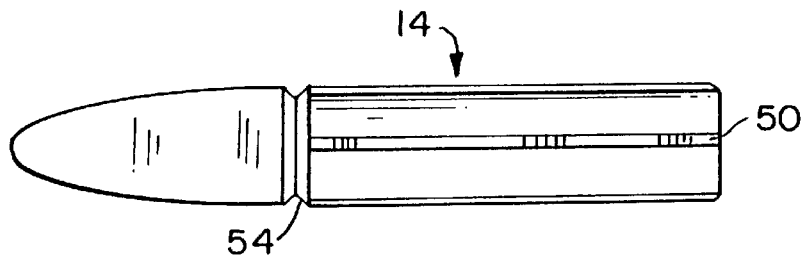
FIG. 8 is a bottom plan view of the cover member shown in FIG. 1.

The cover member 14 of the device 10 cooperates with the dilator member 12 so as to be slidable forwardly and rearwardly along the elongated opening 26. Thus, the cover member 14 closes the first lumen 20 when it is moved toward the front tip 34 and exposes the first lumen 20 when it is moved away from the front tip 34. The cover member 14 is curved so as to be a partial cylinder, as best shown in FIG. 6. At its rear end, the cover member 14 is formed with an outwardly extending flange 44 and the dilator member 12 is similarly formed with an outwardly extending flange 46 at its rear end 22. The flanges 44, 46 function as handles to aid in manipulating the device 10, as will become clear from the following discussion. Although the flanges 44, 46 are shown as being oriented diametrically opposite each other, it is understood that other configurations may be utilized as well.

The outer wall 18 is preferably formed with at least one longitudinally extending rib 48 along its inner surface within the first lumen 20 and the cover member 14 is formed with at least one longitudinally extending rib 50 along its inner surface which extends into the first lumen 20 when the cover member 14 is positioned on the body portion 16 to close the first lumen 20. The ribs 48, 50 provide a sliding surface for the catheter 24 to minimize the surface contact area of the catheter 24 on the device 10 in order to reduce sliding friction.

The guide wall 30 is formed with a recess, or notch, 52 below the forward end 28 of the elongated opening 26. The configuration of the recess 52 and the shape of the forward end of the cover member 14 are such that the forward end of the cover member 14 can be received in the recess 52 when the cover member 14 is moved forwardly and downwardly to close the first lumen 20. However, as is clear from FIG. 2, the recess 52 is aligned with the catheter 24 so that if the cover member 14 were to have its forward end permanently displaced downwardly to fit in the recess 52, when the cover member 14 was slid rearwardly to expose the first lumen 20, its forward end would drag against the catheter 24 and pull it out of the device 10, which is unacceptable. Accordingly, the cover member 14 is formed with a weakened portion 54 which extends laterally across the cover member 14 to act as a resilient hinge and enable the forward end of the cover member 14 to be resiliently flexed downwardly for receipt in the recess 52 of the guide wall 30. Alternatively, the cover member could be formed of a soft resilient plastic which curves downwardly at its forward end. In such case, the recess 52 would not be necessary and the cover member would lightly graze the top of the catheter when it is retracted.

Figure 7:
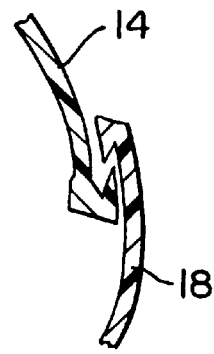
FIG. 7 is a cross sectional detail of the catheterization device shown in FIG. 1 showing the interlocking of the cover member with the dilator member.

To enable the cover member 14 to readily slide along the dilator member 12 and still be held in the proper angular orientation, it is preferred that interlocking features, such as are shown in FIG. 7, be provided at the ends of the cover member 14 and the outer wall 18.

Figure 9:
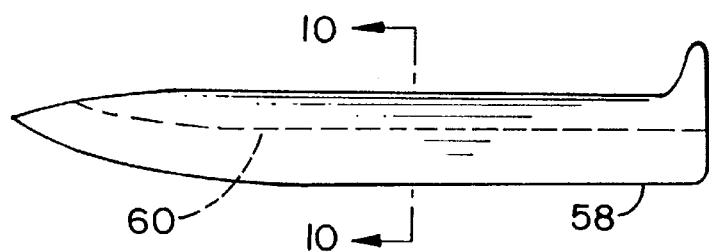
FIG. 9 is a side view of an alternate embodiment of a cover member for use when inserting a guidewire into a blood vessel.
Figure 10:
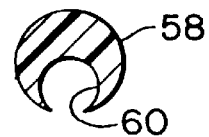
FIG. 10 is a cross sectional view of the alternate embodiment cover member taken along the line 10—10 in FIG. 9.
Figure 11:
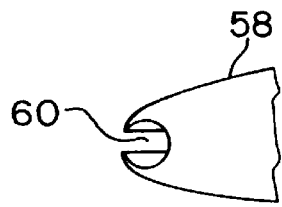
FIG. 11 is a top plan view of the forward portion of the cover member shown in FIG. 9.

When used for inserting the catheter 24 into a patient's blood vessel, the cover member 14 is slid forwardly along the dilator member 12 and its forward end is flexed downwardly for receipt within the recess 52. The needle 40 is then inserted through the second lumen 36 and is used to puncture the patient's skin and blood vessel. The plunger 56 of the syringe 42 is then withdrawn to draw blood from the blood vessel in order to insure that the needle 40 has actually punctured same. By pressing forwardly on the flanges 44, 46, the front tip of the forward portion 32 is used to dilate the puncture hole made by the needle 40 and the device 10 is inserted into the blood vessel for a substantial portion of its length, with the cover member 14 keeping the first lumen 20 closed. The tapered form of the second lumen 36 allows the dilator member 12 to be manipulated relative to the needle 40 during the insertion, so as not to break the fragile needle 40. The catheter 24 is then inserted into the first lumen 20 from the rear end 22 of the dilator member 12, as shown by the solid lines in FIG. 2. The cover member 14 is then slid rearwardly, by gripping the flange 44, to expose the first lumen 20. As the forward end of the cover member 14 exits the recess 52, it snaps upwardly so that it passes over the catheter 24 without dragging it out of the device 10. The catheter 24 is then pushed forwardly and the guide wall 30 guides it out of the device 10 at an angle, as shown by the broken lines in FIG. 2. After a sufficient length of the catheter is inserted into the blood vessel, the dilator member 12 may be withdrawn from the blood vessel, by pulling on the flange 46. The catheter 24 may then be removed laterally from the dilator member 12 through the elongated opening 26. There are times when it is desired to be able to insert a guidewire into a blood vessel. For example, in an angiography procedure, a guidewire is inserted into an artery and advanced through the artery toward the heart. For such a procedure, the cover member 58 (FIGS. 9–11) is used with the dilator member 12. As shown, the cover member 58 fills substantially the entire first lumen 20 and is formed with a third lumen 60 for accepting a guidewire therein. The third lumen 60 is open to the bottom of the cover member 58 and is open at both the front and rear ends of the cover member 58. The forward end of such a guidewire is typically bent into a J-shape and the device with such a guidewire would be packaged with the forward end of the guidewire extending through the open front end of the cover member 58. For insertion of the device into the artery, the guidewire would initially be pulled back slightly so that its forward end is straightened out and retained within the third lumen 60. After insertion of the device into the blood vessel, advancing of the guidewire out of the device results in the forward end returning to its J-shape.

FIGS. 12–14 illustrate a unitary dilator member, designated generally by the reference numeral 70, which has been found to function effectively both with and without a cover. As shown, the dilator member 70 includes a main portion 72 which is hollow and substantially cylindrical and defines a major central axis 74. Along the length of the outer wall of the main portion 72, there is a continuous opening 76 which exposes the interior 78 of the main portion 72. As with the previously described embodiment, the interior 78 is adapted to receive a catheter or other elongated member therein and is sized to allow the received catheter to move longitudinally therein. At its forward end, the interior 78 has a guide wall 80 which is transverse to the axis 74 and which ascends obliquely from the lower end of the interior 78 to where it passes beyond the opening 76. While the interior 78 is sized to allow a catheter to move longitudinally therein, it subtends an arc which is such that the width of the opening 76 is less than the diameter of the received catheter. Preferably, the subtended arc is in the range from about 190° to about 220°. Thus, a catheter is retained within the interior 78 without requiring a cover. However, since the outer wall of the main portion 72 is relatively thin and the dilator member 70 is formed of plastic material which is resilient, when the catheter is pushed forwardly and then directed upwardly by the guide wall 80, the outer wall of the main portion 72 spreads sufficiently so that the catheter can exit the interior 78.

The dilator member 70 further includes a forward portion 82 at an end of the main portion 72 beyond the guide wall 80. The forward portion 82 tapers inwardly away from the main portion 72 to a front tip 84. The forward portion 82 has a lateral portion 86 which extends laterally beyond an axial projection of the main portion 72, as best shown in FIG. 14. The lateral portion 86 also tapers toward the front tip and is formed with a lumen 88 adapted for receiving a needle therein. The lumen 88 has a forward opening 90 adjacent the front tip 84 and a rear opening 92 beyond the main portion axial projection. Preferably, the front tip 84 is offset from the axis 74 toward the lumen 88, as shown in FIG. 13. Further, the main axis of the lumen 88 is substantially parallel to the axis 74 so that when a needle is inserted in the lumen 88 from the rear opening 92 with its forward tip extending beyond the forward opening 90, the rear of the needle is laterally adjacent the main portion 72.

To aid in manipulating the dilator member 70, at its end opposite the forward portion 82, the dilator member 70 is formed with a flange 94, 96 extending outwardly from the outer wall of the main portion 72 and orthogonal to the axis 74. The flange 94, 96 acts as a handle to aid in inserting the dilator member into a blood vessel and removing the dilator member 70 from the blood vessel. Preferably, the flange 94, 96 is split to provide a gap 98 overlying the opening 76 and extending to the bottom of the interior 78 of the main portion 72. The overall length of the dilator member 70, from the front tip 84 to the flange 94, 96, is preferably about four inches (100 mm).

FIG. 15 illustrates a cover member, designated generally by the reference numeral 100, which may be utilized with the dilator member 70. The cover member 100 has an elongated body portion 102 shaped as a partial cylinder and sized to fit within the interior 78 of the dilator member main portion 72 for longitudinal movement therein while overlying a catheter or other elongated member received in the interior 78. A handle portion 104 is secured to the body portion 102 at its rearward end. The handle portion 104 is shaped as a planar fin in the plane containing the axis 74 (when the cover member 100 is installed) and is so located angularly on the body portion 102 that when the body portion 102 is moved longitudinally within the interior 78 of the main portion 72 of the dilator member 70, the handle portion 104 passes through the gap 98 of the split flange 94, 96.

In use, a catheter or other elongated member is installed within the interior 78 of the dilator member main portion 72, with the forward end of the catheter being spaced from the guide wall 80 so that the catheter lies flat within the interior 78. A needle is then inserted through the lumen 88 and the rear of the needle is held next to the main body portion 72 of the dilator member 70 by a syringe or other holding device. When inserting a catheter into a blood vessel, a hypodermic syringe needle may be used and the needle is inserted through the patient's skin into the blood vessel. The plunger of the syringe is withdrawn slightly to insure that the needle has actually entered the blood vessel. Either before or after the needle puncture, a small incision is made in the patient's skin through the puncture. The front tip 84 of the dilator member 70 is then pushed through the incision and, following the needle, through the punctured wall of the blood vessel, enlarging the puncture hole formed by the needle. The dilator member 70 is then pushed forwardly until the needle comes out of the lumen 88 and a portion of the dilator member 70 rearwardly of the guide wall 80 is within the blood vessel. The needle is then removed from the patient. If the cover member 100 had been utilized, it is then withdrawn. The catheter is then pushed forwardly and the guide wall 80 directs the catheter upwardly to spread the outer walls of the main portion 72 so that the catheter laterally exits the interior 78 and enters the patient's blood vessel. The dilator member 70 is then withdrawn from the patient's body and moved laterally with respect to the catheter so that the catheter is freed from the interior 78. The dilator member 70, along with the cover member 100 if used, and the needle are then disposed of and the catheter is utilized in its usual manner.

Modifications to the disclosed devices are possible. For example, the cover member could extend outside the dilator member, instead of inside as shown. Also, the elongated opening of the dilator member could be along its bottom or side, not necessarily opposite the needle, or could even follow a spiral path as it extends from the forward guide wall toward the rear of the dilator member. The dilator device can also be constructed without the guide wall, so that the catheter exits the device axially (i.e., the lumen containing the catheter is open both at its front and rear). Further, although the present invention has been specifically illustrated as a device for inserting a catheter into a patient's blood vessel, the inventive device can be used to insert a catheter into other body conduits as well, such as a patient's trachea. Still further, the inventive device can be used to insert a catheter into other parts of a human body as well, such as into a muscle, into the bladder, or into any other internal organ which may require the insertion of a catheter. Other elongated members, such as guidewires, optical fibers, stents, etc., can also be inserted into a body by using the inventive device.

Accordingly, there have been disclosed improved devices for both dilating a needle puncture hole in a body and for subsequently providing a guide for the insertion of a catheter or other elongated member into the body through the puncture hole. These devices eliminate the need for a disposable guidewire and also allow the use of a relatively small needle, thereby minimizing damage to the wall of the body conduit. While alternate embodiments of the present invention have been disclosed herein, it will be apparent to one of ordinary skill in the art that various modifications and adaptations to the disclosed embodiments are possible and it is intended that this invention be limited only by the scope of the appended claims.

What is claimed is:

1. A device in the form of a unitary dilator member comprising:
   an elongated body portion with an outer wall defining a substantially uniform first lumen adapted for receiving a catheter or the like therein, the body portion having an elongated opening longitudinally disposed in said outer wall and communicating with said first lumen; and
   a forward portion extending forwardly of said body portion and tapering inwardly to a front tip, the forward portion having a second lumen axially offset from the first lumen and adapted for receiving a needle therein with the forward tip of the needle extending forwardly of the front tip and the rear of the needle extending rearwardly alongside the dilator member body portion.

2. The device according to claim 1 wherein said second lumen is tapered inwardly toward said front tip.

3. The device according to claim 1 wherein:
   said dilator member body portion is formed with a flange extending outwardly from said outer wall adjacent said body portion rear end to act as a handle for inserting said device into a blood vessel and for retracting said dilator member from said blood vessel.

4. The device according to claim 1 wherein a substantial portion of the length of said body portion forwardly from its rear end is substantially cylindrical and said forward portion of said dilator member extends beyond an axial projection of the cylindrical body portion, at least the lateral opening of said second lumen being in that part of said forward portion which extends beyond said axial projection.

5. The device according to claim 4 wherein said forward portion of said dilator member extends to the opposite side of said dilator member from said elongated opening.

6. The device according to claim 1 wherein said first lumen has a circular arcuate shape in cross-section with a diameter sufficiently larger than the diameter of a catheter received therein so that the received catheter has sufficient clearance to move longitudinally within said first lumen, the angle subtended by said first lumen being such that the width of said elongated opening is less than the diameter of the received catheter.

7. The device according to claim 1 wherein said second lumen is substantially parallel to said first lumen.

8. The device according to claim 1 wherein said first lumen is open at the rear end of said body portion and the forward end of said first lumen is terminated by a guide wall extending from the bottom of said first lumen opposite said elongated opening and ascending obliquely toward the forward end of said elongated opening.

9. A unitary dilator member for use in inserting a catheter or the like into a body, the dilator member comprising:
   a hollow substantially cylindrical main portion defining a major central axis and having along the length of its outer wall a continuous opening exposing the interior of said main portion, wherein the interior of said main portion is adapted to receive a catheter or the like therein and is sized to allow the catheter to move longitudinally therein; and
   a forward portion at an end of said main portion, said forward portion tapering inwardly away from said main portion to a front tip, said forward portion having a lateral portion extending laterally beyond an axial projection of said main portion, said lateral portion tapering toward said front tip and having a lumen adapted for receiving a needle therein, said lumen having a forward opening adjacent said front tip and a rear opening beyond said main portion axial projection;
   whereby when a needle is inserted in the lumen from the lumen rear opening with its forward tip extending beyond the lumen forward opening, the rear of the needle is laterally adjacent the main portion.

10. The dilator member according to claim 9 wherein the angle subtended by the outer wall is such that the width of the opening is less than the diameter of the received catheter.

11. The dilator member according to claim 9 wherein the forward end of the interior of said main portion is terminated by a guide wall transverse to said major central axis and ascending obliquely toward the forward end of said continuous opening.

12. The dilator member according to claim 9 wherein the front tip of said forward portion is offset from said major central axis of said main portion toward said lumen.

13. The dilator member according to claim 9 further including a flange extending outwardly from the outer wall of said main portion orthogonal to said major central axis to act as a handle to aid in inserting and removing said dilator member with respect to said conduit.

14. The dilator member according to claim 13 wherein said flange has a separation to provide a gap overlying said continuous opening of said main portion.

15. A unitary cover member for use with the unitary dilator member according to claim 14, comprising:

an elongated body portion shaped as a partial cylinder and sized to fit within the interior of said dilator member main portion for longitudinal movement therein while overlying a catheter or the like received therein; and a handle portion secured to said body portion, said handle portion being shaped as a planar fin in a plane containing said major central axis and located angularly on said body portion so that when said body portion is moved longitudinally within the interior of said dilator member main portion the handle portion passes through the gap of said flange.

* * * * *